United States Patent [19]
Fauchere et al.

[11] Patent Number: 5,565,426
[45] Date of Patent: Oct. 15, 1996

[54] PEPTIDE COMPOUNDS ACTIVE IN CELL ADHESION PROCESSES

[75] Inventors: Jean-Luc Fauchere, Saint-Cloud; Angela D. Morris, Viroflay; Christophe Thurieau, Paris; Tony Verbeuren, Vernouillet; Serge Simonet, Conflans-St-Honorine, all of France

[73] Assignee: Adir et Compagnie, Courbevoie, France

[21] Appl. No.: 288,984

[22] Filed: Aug. 11, 1994

Related U.S. Application Data

[63] Continuation of Ser. No. 84,702, Jun. 23, 1993, abandoned.

[30]     Foreign Application Priority Data

Jun. 30, 1992 [FR] France .................... 92 08004

[51] Int. Cl.$^6$ .................................................. A61K 38/07
[52] U.S. Cl. ............................. 514/17; 530/330; 530/332; 514/18
[58] Field of Search ................. 514/18; 530/330

[56]         References Cited

FOREIGN PATENT DOCUMENTS 0275748  7/1988  European Pat. Off. .......... C07K 7/06
0341915  11/1989  European Pat. Off. .......... C07K 5/00

OTHER PUBLICATIONS

TIPS 13, 413–417 (1992).
J. Pharmacol. Exp. Therap. 225, No. 1, 57–60 (1983).
Adv. Exp. Med. Biol. 180, 635–649 (1984).
Hermanson "Immobilized Affinity Ligand Techniques" Academic Press 1992.

*Primary Examiner*—Elizabeth C. Weimar
*Assistant Examiner*—David Lukton
*Attorney, Agent, or Firm*—The Firm of Gordon W. Hueschen

[57]             ABSTRACT

The invention relates to peptide compounds of formula (I):

$$R_1\text{—}A\text{—}Gly\text{—}Asp\text{—}Trp\text{—}R_2 \qquad (I)$$

in which $R_1$, $R_2$ and A are as defined in the description, and anti-aggregation medicaments containing the same.

12 Claims, No Drawings

PEPTIDE COMPOUNDS ACTIVE IN CELL ADHESION PROCESSES

This application is a continuation of application Ser. No. 08/084,702, filed Jun. 23, 1993, now abandoned.

BACKGROUND OF THE INVENTION

The present invention relates to new peptide compounds, a process for the preparation thereof and pharmaceutical compositions containing them. The compounds of the present invention have a valuable pharmacological use as platelet anti-aggregation agents.

It is known that the prevention of thrombosis and atherosclerosis is dependent on the control and regulation of platelet aggregation. The formation of a thrombus or blood clot is linked with the presence of fibrinogen which, as a result of its interaction with a specific receptor, causing cell adhesion, participates in platelet aggregation. The mechanism is general for all inducers and it is therefore particularly valuable to seek to regulate or inhibit fibrinogen-dependent aggregation.

Peptide compounds possessing anti-aggregation properties are already known. There may be mentioned by way of example:

patent EP-A-319506 where the following peptide chain is found:

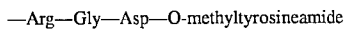
—Arg—Gly—Asp—O-methyltyrosineamide patent U.S. Pat. No. 4,578,079 which describes peptides having the formula:

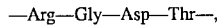
—Arg—Gly—Asp—Thr—,

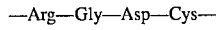
—Arg—Gly—Asp—Cys— or

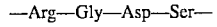
—Arg—Gly—Asp—Ser— and patent EP-A-220957 disclosing peptides having the formula:

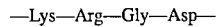
—Lys—Arg—Gly—Asp— or

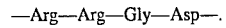
—Arg—Arg—Gly—Asp—.

Patents EP-A-275748 and EP-A-341915 propose tetrapeptides having the formula $X_1$—Arg—Gly—Asp—Trp—$X_2$ in which $X_1$ and $X_2$ may be residues of natural amino acids.

SUMMARY OF THE INVENTION

The present invention relates to peptide compounds that are novel compared with the compounds described in the prior art. The intensity of the pharmacological properties of the products of the invention has been optimised by modifying the length and the nature of the N-terminal substituent of the tetrapeptide.

More especially, the invention relates to new peptide compounds corresponding to the general formula (I):

$$R_1—A—Gly—Asp—Trp—R_2 \quad (I)$$

in which:

A represents an arginine (Arg) or lysine (Lys) residue, $R_1$ represents a linear, branched or cyclic amino acid residue, the amine grouping of which is not in the α-position relative to the carbonyl grouping, and $R_2$ is chosen among —$NH_2$ and —OH, their stereoisomers and also their addition salts with a pharmaceutically acceptable acid or base, it being understood that each amino acid of the peptide sequence is optically pure and may have the D or L configuration.

The linear, branched or cyclic amino acid residues, the amine grouping of which is not in the α-position, are amino acid residues preferably selected, in a non-limiting manner, from 3-aminopropanoic acid, 3-amino-2-methylpropanoic acid, 4-aminobutanoic acid, 5-aminopentanoic acid, 6-aminohexanoic acid, 7-aminoheptanoic acid, pyrrolidine-3-carboxylic acid, piperidine-4-carboxylic acid, pyridine-4-carboxylic acid and quinoline-4-carboxylic acid.

The invention extends also to a process for the preparation of the compounds of formula (I) which can be obtained by various methods, such as sequential solid-phase synthesis, synthesis of fragments and their coupling in solution, enzymatic synthesis, genetic synthesis by cloning and expression of genes in transformed bacteria or by various combinations of those techniques.

The peptides of the present invention are generally obtained by solid-phase synthesis according to the method described by B. W. ERICKSON and R. B. MERRIFIELD ("The Proteins", solid-phase peptide synthesis, 3rd edition, 257–527, 1976).

More specifically, the process for the preparation of the compounds of the invention follows the method of synthesis and coupling of fragments in a solid phase.

The solid phase may be one of the polymeric resins customarily used, such as, for example, a polystyrene crosslinked by divinylbenzene (1 to 2%) on which a linker, for example p-alkoxybenzyl alcohol or benzhydrylamine, is fixed, to which linker the peptide is attached in the course of the coupling of amino acids and which permits, at the end of the synthesis, the freeing of an acid, amide, alcohol or other C-terminal function.

The list of abbreviations used in the following synthesis process is given in the annex.

The process for the preparation of the products of the invention is characterised in that each stage of the synthesis is composed of two operations, namely:

1) deprotection of the substrate by means of a suitable base, such as, for example, piperidine, 2) coupling of a protected amino acid in the presence of a coupling reagent customarily used in peptide synthesis, such as, for example, the pair DCC/HOBT, TBTU/DIEA, BOP/DIEA or DPPA, the reagents and substrates obtained for each stage being:

| Stage | coupling reagent | | Substrate obtained | |
| --- | --- | --- | --- | --- |
| 0 | | | P₁—Ⓡ | (II) |
| 1 | P₁—Trp—OH | (III) | P₁—Trp—Ⓡ | (VIII) |
| 2 | P₁—Asp(P₂)—OH | (IV) | P₁—Asp(P₂)—Trp—Ⓡ | (IX) |
| 3 | P₁—Gly—OH | (V) | P₁—Gly—Asp(P₂)—Trp—Ⓡ | (X) |
| 4 | P₁—A(P₃)—OH | (VI) | P₁—A—Gly—Asp(P₂)—Trp—Ⓡ | (XI) |
| 5 | P₁—R₁—OH | (VII) | P₁—R₁—A—Gly—Asp(P₂)—Trp—Ⓡ | (XII) | in which compounds of formulae (II) to (XII):

$R_1$ and A are as defined above,

Ⓡ represents the resin support, $P_1$ is a protecting grouping, such as, for example, Fmoc or Boc, $P_2$ is an aspartic acid protecting grouping, such as, for example, OtBu or Bzl, $P_3$ is a protecting grouping, for example Pmc in the case of arginine or Boc in the case of lysine, which compounds of formula (XII) are then freed from the resin support and amino acid protecting groups by a mixture of TFA, ethane-1,2-dithiol, anisole and optionally DCM, the aspartic acid protecting grouping, when it is Bzl, being eliminated by treatment with ammonium hydrogen carbonate and palladium in methanol, finally to yield the crude peptides of formula (I) which are purified by a conventional purification technique and which are converted, where appropriate, into their addition salts with a pharmaceutically acceptable acid or base.

The compounds of the present invention have anti-aggregation properties and can be used in cases of thromboembolism for dissolving blood clots or as agents preventing the spread of the thrombotic process by using them as anticoagulants having direct and rapid action, or in any other pathological situation involving cell adhesion processes.

They will therefore prove to be effective in the treatment of thromboses, pulmonary embolism, arterial embolism of the extremities, atherosclerosis and thrombolytic symptoms, and also myocardial infarct and in the treatment of restenoses after angioplasty, and also in the maintenance of blood homoeostasis, especially in extracorporeal circulation.

The present invention relates also to pharmaceutical compositions containing as active ingredient at least one compound of the general formula (I) or one of its addition salts with a pharmaceutically acceptable acid or base, alone or in combination with one or more inert, non-toxic excipients or carriers.

Of the pharmaceutical compositions of the invention, there may be mentioned more especially those that are suitable for administration by the oral, parenteral or nasal route, tablets, dragées, sublingual tablets, sachets, packets, gelatin capsules, glossettes, lozenges, suppositories, creams, ointments, dermal gels and aerosols.

The dosage varies according to the age and weight of the patient, the nature and severity of the disorder and also according to the mode of administration. The latter may be oral, nasal, rectal or parenteral. In general, it ranges from 0.2 to 100 mg for a treatment in one or several doses per 24 hours.

DESCRIPTION OF THE PREFERRED EMBODIMENTS

Abbreviations Used in the Present Invention

Boc: tert-butoxycarbonyl

BOP: benzyloxytriazol-1-oxytrisdimethylaminophosphonium hexafluorophosphate

Bzl: benzyl

DCC: 1,3-dicyclohexylcarbodiimide

DCM: dichloromethane

DIEA: diisopropylethylamine

DMF: dimethylformamide

DPPA: diphenylphosphorylazide

Fmoc: 9-fluorenylmethylcarbonyl

HOBT: 1-hydroxybenzotriazole

Pmc: 2,2,5,7,8-pentamethylchroman-6-sulphonyl

OtBu: β-tert-butyl ester

TFA: trifluoroacetic acid

The following Examples illustrate the invention and do not limit it in any way.

EXAMPLE 1

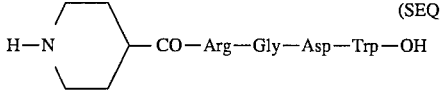

(SEQ ID NO: 1)

2.0 g of Fmoc-Trp, fixed on an ester resin by means of a p-alkoxybenzyl alcohol grouping, are stirred with 30 ml of a 20 % by volume solution of piperidine in dimethylformamide for 30 minutes in order to free the tryptophan of its protecting grouping. The mixture is filtered and the resin is washed with the solvents DMF and DCM. The deprotected fragment is subjected to 1.81 g of Fmoc—Asp(OtBu)—OH in 30 ml of DMF in the presence of 997 mg of DCC and 743 mg of HOBT for 3 hours. After filtering and washing with DMF, isopropyl alcohol and DCM, the medium is treated as above with a 20% solution of piperidine in DMF. The substrate is then treated in the same manner with 1.308 g of Fmoc—Gly—OH and then 2.916 g of Fmoc—Arg(Pmc)—OH and finally with 1.492 g of Fmoc-(isonipecotic acid) (synthone prepared in accordance with the procedure described by Carpino and Han (*J. Org. Chem.*, 1972, 37, 3404)). The peptide is then detached from the resin support and freed of protecting groupings by treatment with a mixture of 16 ml of trifluoroacetic acid, 2 ml of anisole, 2 ml of ethanedithiol and 4 ml of DCM for two hours at ambient temperature. After filtration and concentration of the filtrate, the residue is triturated in diethyl ether and then filtered to give the expected crude peptide. The crude product is purified by reverse phase liquid chromatography (column c 18, gradient 10–35% of $CH_3CN$ in 25 minutes) to yield, after lyophilisation, the corresponding ditrifluoroacetate.

Mass spectrum (FAB): $[M+H]^+$: m/z=644 (molecular weight: 643).

The compounds of the Examples below were prepared in accordance with the same procedure as that described in Example 1 with the following modifications:

when arginine is replaced by lysine, the reagent used is Fmoc—Lys(Boc)—OH instead of Fmoc—Arg(Pmc)—OH.

the "amide" end group of tryptophan is obtained by using a resin of the type 2,4-dimethoxy-4'-(carboxymethoxy-)benzhydrylamine from which the peptide-amide is freed at the end of the synthesis by treatment with trifluoroacetic acid.

Fmoc (isonipecotic acid) is replaced by the corresponding amino residue, still protected by Fmoc.

EXAMPLE 2

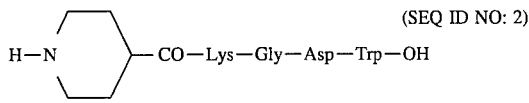
(SEQ ID NO: 2)

EXAMPLE 3

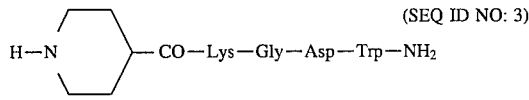
(SEQ ID NO: 3)

Mass spectrum: (FAB): $[M+H]^+$: m/z=615 (molecular weight: 614.7).

EXAMPLE 4

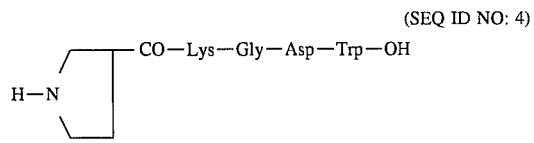
(SEQ ID NO: 4)

EXAMPLE 5

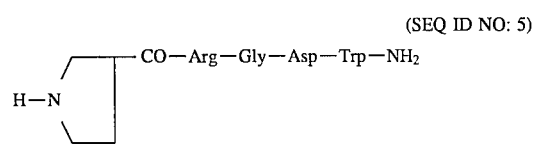
(SEQ ID NO: 5)

EXAMPLE 6

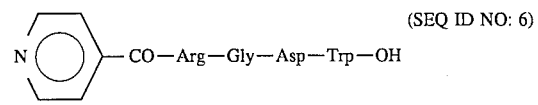
(SEQ ID NO: 6)

Mass Spectrum: (FAB): $[M+H]^+$: m/z=638 (molecular weight: 637.6).

EXAMPLE 7

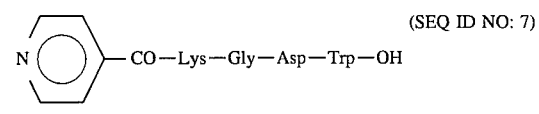
(SEQ ID NO: 7)

Mass spectrum: (FAB): $[M+H]^+$: m/z=610 (molecular weight: 609.6).

EXAMPLE 8

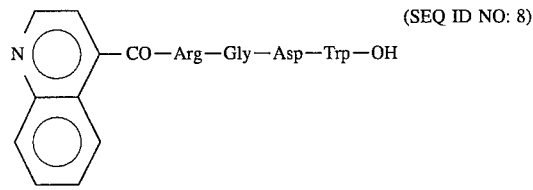
(SEQ ID NO: 8)

Mass spectrum: (FAB): $[M+H]^+$: m/z=688 (molecular weight: 687.7).

EXAMPLE 9

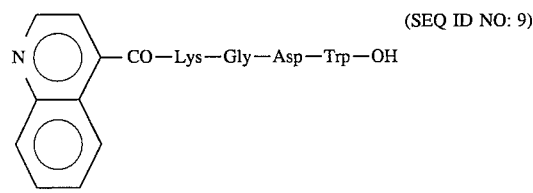
(SEQ ID NO: 9)

Mass spectrum: (FAB): $[M+H]^+$: m/z=660 (molecular weight: 659.7).

EXAMPLE 10

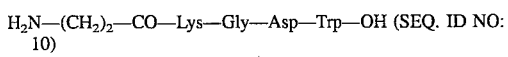
$H_2N-(CH_2)_2-CO-Lys-Gly-Asp-Trp-OH$ (SEQ. ID NO: 10)

EXAMPLE 11

$H_2N-(CH_2)_3-CO-Arg-Gly-Asp-Trp-OH$ (SEQ. ID NO: 11)

Mass spectrum: (FAB): $[M+H]^+$: m/z=618 (molecular weight: 617).

EXAMPLE 12

$H_2N-(CH_2)_3-CO-Lys-Gly-Asp-Trp-OH$ (SEQ. ID NO: 12)

Mass spectrum: (FAB): $[M+H]^+$: m/z=590 (molecular weight: 589).

EXAMPLE 13

$H_2N-(CH_2)_4-CO-Arg-Gly-Asp-Trp-OH$ (SEQ. ID NO: 13)

Mass spectrum: (FAB): $[M+H]^+$: m/z=632 (molecular weight: 631).

EXAMPLE 14

$H_2N-(CH_2)_5-CO-Arg-Gly-Asp-Trp-OH$ (SEQ. ID NO: 14)

Mass spectrum: (FAB): $[M+H]^+$: m/z=646 (molecular weight: 645).

EXAMPLE 15

$H_2N-(CH_2)_5-CO-Lys-Gly-Asp-Trp-OH$ (SEQ. ID NO: 15)

EXAMPLE 16

$H_2N-(CH_2)_5-CO-Lys-Gly-Asp-Trp-NH_2$ (SEQ. ID NO: 16)

Mass spectrum: (FAB): [M+H]⁺: m/z=617 (molecular weight: 616.7).

EXAMPLE 17

H₂N—(CH₂)₆—CO—Arg—Gly—Asp—Trp—OH (SEQ. ID NO: 17)

Mass spectrum: (FAB): [M+H]⁺: m/z=660 (molecular weight: 659).

EXAMPLE 18

H₂N—(CH₂)₆—CO—Lys—Gly—Asp—Trp—NH₂ (SEQ. ID NO: 18)

EXAMPLE 19

H₂N—(CH₂)₇—CO—Arg—Gly—Asp—Trp—NH₂ (SEQ. ID NO: 19)

EXAMPLE 20

H₂N—CH(CH₃)—CO—Arg—Gly—Asp—Trp—OH (SEQ. ID NO: 20)

PHARMACOLOGICAL STUDY

EXAMPLE 21

Platelet Aggregation

The study is carried out on canine platelets. After anaesthetising the animal with pentobarbitone sodium (30 mg/kg i.v.), the arterial blood is withdrawn onto sodium citrate (0.109M) (11 vol. of citrate per 9 vol. of blood). The platelet-rich plasma (PRP) is obtained after centrifugation (20° C.) at 200 g for 10 minutes. The number of platelets in the PRP is on average 300,000 pl/mm³· The PRP is maintained at room temperature until the time of the test and is used within the 4 hours following removal.

The anti-aggregation effect of the products is examined on platelets activated by adenosine diphosphate (ADP) (10 $\mu$M). The platelet aggregation is carried out at 37@C in silicone glass tubes using an aggregometer (Coultronics). The PRP is stirred at 1000 rpm. In order to test the effect of the antagonist, the PRP is incubated with the substance for 9 minutes without stirring and for 1 minute with stirring. The ADP (10 $\mu$M) is then added.

The effect of the antagonists is measured and the IC₅₀ is determined as the concentration of the antagonist necessary to produce 50% inhibition of the aggregating responses with ADP. The results are reproduced in the following Table I:

TABLE I

| | Inhibition of platelet aggregation attributable to fibrinogen |
|---|---|
| | IC₅₀ ($\mu$M) |
| Example N° | |
| Example 1 | 0.23 |
| Example 11 | 2.1 |
| Example 12 | 2.3 |

TABLE I-continued

| | Inhibition of platelet aggregation attributable to fibrinogen |
|---|---|
| | IC₅₀ ($\mu$M) |
| Example 13 | 2.4 |
| Example 14 | 0.79 |
| Example 17 | 6.3 |
| Reference compounds | |
| Acétyl-cyclo(Cys—Arg—Gly—Asp—Pen)NH₂* | 8.1 |
| H—Arg—Gly—Asp—OH** | 22.6 |

*Product described in EP-A-341915
**Product described in EP-A-275748

EXAMPLE 22

Experimental Thrombosis in the Mesenteric Artery of the Rat

The experiments were carried out on male rats (250 to 400 g). The animals are anaesthetised with pentobarbitone (50 mg/kg i.p.). A catheter is installed in the jugular vein in order to permit i.v. injections.

The preparation of the mesenteric artery and the induction of thrombosis are carried out in accordance with the method described by Bourgain et al. *Adv. Exp. Med. Biol.*, 180, 635–649, (1984). A longitudinal incision is made in the abdomen and part of the intestine is exposed. Using a binocular magnifying device, a branch of the mesenteric artery from 200 to 500 $\mu$m in diameter is prepared. The adjacent vein is separated and the adipose tissues are removed; a 2 mm segment of artery is thus prepared. The animal is then installed under a microscope and the segment of the mesenteric artery is perfused with physiological solution (37° C.) at 5 ml/min. The segment can be observed for several hours. The images are recorded using a video camera and a magnetoscope.

After installation and stabilisation of the preparation, a platinum electrode is placed on each side of the arteriole wall using a micromanipulator. An endothelial lesion is then induced by applying for 60 seconds an electric current of 40 $\mu$A, the current being reversed every 5 seconds. The lesion is slight and does not bring about any change in the blood flow or in the diameter of the vessel. Normally, no thrombus formation is observed on applying the electric current.

The formation of a clot is then induced by perfusion with ADP (adenosine diphosphate) for 2 minutes. The ADP is used at a final molarity of 300 $\mu$M. The clot forms and then, after 2 to 5 minutes, disappears by embolisation. The vessel then re-assumes a normal state; there is no spontaneous formation of a clot. Every 15 minutes, the perfusion with ADP can be repeated and the clots which are formed are of a comparable size.

The effect of the products on the formation of thrombi was tested by treating the animals by venous infusion for 5 minutes. The infusion starts ! minute before perfusion with ADP.

The recorded images are analysed and the size of the clots is expressed in arbitrary surface values. The measurements are carried out at determined times during and after the perfusion of ADP. A comparison can therefore be made of the size of the clots in the control state and after the infusion of the product.

The results are given in the following Table II:

TABLE II

Percentage inhibition of the formation of a blood clot in the mesenteric artery of the rat

| COMPOUNDS | % INHIBITION Infusion for 5 min | | |
|---|---|---|---|
| | 2 mg/ kg/min | 5 mg/kg/min | 10 mg/ kg/min |
| Example 12 | 17 | 33 | 56 |
| H—Arg—Gly—Asp—Trp—OH (EP-A-275748) | — | — | 36 |

EXAMPLE 23

Thromboembolism in Mice

Male mice (CD-1) weighing from 28 to 32 g are used for these experiments. The animals are maintained at from 26° to 28° C. for the 30 minutes preceding the experiment. A combination of collagen (150 µg/ml) and adrenaline (100 µmol/l) causes the mice to die by paralysis. Each mouse receives 0.1 ml of that combination, which gives a dose of 1.8 µg of adrenaline and 15 µg of collagen per mouse. The incidence of death or paralysis is observed 15 minutes after the intravenous injection (i.v.) of the combination (adrenaline+collagen) into the caudal vein. The peptides are injected at the same time as the combination of agonists. In the case of the tests relating to the duration of action, the mice are pre-treated with the peptides i.v. in a volume of 0.1 ml. A histological examination of the lungs is carried out in order to visualise the presence of microthrombi in the vessels of the microcirculation, which are attributable to the adrenaline-collagen combination. At the end of the experiment, the lungs are rapidly removed, fixed in formalin and then enclosed in paraffin. 5 µm sections are made and coloured with haematoxylin/eosin. The sections are examined and the presence or absence of microthrombi is noted. The $X^2$ test (Fischer) is used to determine whether there is a significant difference between the effects in mice that have received the peptides and those that have not.

The compounds of the invention are active in this test and protect the mice against the effects of collagen and adrenaline; for example, the compound of Example 11 protects half of the mice at a dose of 0.03 mg/mouse and is 10 times more active than the reference substance (RDGW=H—Arg—Gly—Asp—Trp—OH (EP-A-275748)) which protects only half of the mice at a dose of 0.3 mg/mouse. In addition, the duration of action of RGDW at a dose of 1 mg is less than 5 minutes while in the case of the compounds of the invention, such as, for example, the compound of Example 1, it is more than one hour. The formation of microthrombi in the lungs is inhibited to a greater extent with the compounds of the invention than with RGDW. For example, the compound of Example 11 inhibits the formation of thrombi in a significant manner from a dose of 0.03 mg/mouse. RGDW is active only from a dose of 1 mg/mouse.

We claim:

1. A compound of formula (I):

R₁—A—Gly—Asp—Trp—R₂   (I)

in which:

A represents an arginine (Arg) or lysine (Lys) residue,

R₁ represents an amino acid residue selected from the group consisting of piperidine-4-carboxylic acid, and R₂ is chosen from —NH₂ and —OH, or a stereoisomer thereof or a pharmaceutically-acceptable salt thereof.

2. A compound according to claim 1 in which A represents an arginine residue (Arg).

3. A compound according to claim 1 in which A represents a lysine residue (Lys).

4. A compound according to claim 1 in which R₂ represents —OH.

5. A compound according to claim 1 which is

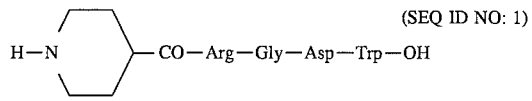
(SEQ ID NO: 1)

6. A compound according to claim 1 which is

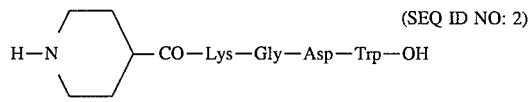
(SEQ ID NO: 2)

7. A pharmaceutical composition useful as an anti-aggregation agent or for inhibition of blood clotting, which contains as active ingredient an effective amount of a compound of formula (I):

R₁—A—Gly—Asp—Trp—R₂   (I)

in which:

A represents an arginine (Arg) or lysine (Lys) residue,

R₁ represents an amino acid residue selected from the group consisting of piperidine-4-carboxylic acid, pyrrolidine-3-carboxylic acid, 4-aminobutanoic acid, 5-aminopentanoic acid, 6-aminohexanoic acid, 7-aminoheptanoic acid, and 8-aminooctanoic acid, and R₂ is chosen from —NH₂ and —OH, or a stereoisomer thereof or a pharmaceutically-acceptable salt thereof, in combination with one or more pharmaceutically-acceptable excipients or vehicles.

8. A composition of claim 7 wherein R₁ represents 6-aminohexanoic acid or piperidine-4-carboxylic acid.

9. A composition of claim 7 wherein the compound is

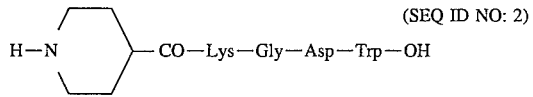
(SEQ ID NO: 2)

10. A method for treating a mammal afflicted with a disease requiring an anti-aggregation agent for inhibition of blood clotting comprising the step of administering to the said mammal an amount of a compound of formula (I)

R₁—A—Gly—Asp—Trp—R₂   (I)

in which:

A represents an arginine (Arg) or lysine (Lys) residue,

R₁ represents an amino acid residue selected from the group consisting of piperidine-4-carboxylic acid, pyrrolidine-3-carboxylic acid, 4-aminobutanoic acid, 5-aminopentanoic acid, 6-aminohexanoic acid, 7-aminoheptanoic acid, and 8-amino-octanoic acid, and R₂ is chosen from —NH₂ and —OH, or a stereoisomer thereof or a pharmaceutically-acceptable salt thereof, which is effective for such purpose.

11. A method of claim 10 wherein R₁ represents 6-aminohexanoic acid or piperidine-4-carboxylic acid.

12. A method of claim 10 wherein the compound is

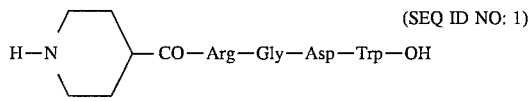
(SEQ ID NO: 1)

* * * * *

UNITED STATES PATENT AND TRADEMARK OFFICE
CERTIFICATE OF CORRECTION

PATENT NO. : 5,565,426
DATED : Oct. 15, 1996
INVENTOR(S) : J. Fauchere; A. Morris; C. Thurieau; T. Verbeuren; S. Simonet It is certified that error appears in the above-indentified patent and that said Letters Patent is hereby corrected as shown below:

Column 5, line 2: Delete the dash at the end of the line and insert -- ) --.

Column 5, line 3: Delete ")" from the beginning of the line.

Column 7, line 24: "$H_2N-CH(CH_3)-$" should read: -- $H_2N-CH_2-CH(CH_3)-$ --.

Column 24, line 27: Insert -- or -- after the word "agent".

Signed and Sealed this

Twenty-eighth Day of January, 1997

Attest:

BRUCE LEHMAN

Attesting Officer   Commissioner of Patents and Trademarks

SEQUENCE LISTING ( 1 ) GENERAL INFORMATION:

( i i i ) NUMBER OF SEQUENCES: 20

( 2 ) INFORMATION FOR SEQ ID NO:1:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( i i ) MOLECULE TYPE: peptide ( i x ) FEATURE:
( A ) NAME/KEY: Modified-site
( B ) LOCATION: 1
( D ) OTHER INFORMATION: /note="piperidine-4-carboxylic acid"

( i x ) FEATURE:
( A ) NAME/KEY: Modified-site
( B ) LOCATION: 6
( D ) OTHER INFORMATION: /label=OH ( x i ) SEQUENCE DESCRIPTION: SEQ ID NO:1:

Xaa Arg Gly Asp Trp Xaa
1               5

( 2 ) INFORMATION FOR SEQ ID NO:2:

( i ) SEQUENCE CHARACTERISTICS:
( A ) LENGTH: 6 amino acids
( B ) TYPE: amino acid
( C ) STRANDEDNESS: single
( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note="SEE SEQ ID NO:1"

( i x ) FEATURE:
    ( A ) NAME/KEY: Modified-site
    ( B ) LOCATION: 6
    ( D ) OTHER INFORMATION: /label=OH ( x i ) SEQUENCE DESCRIPTION: SEQ ID NO:2:

Xaa Lys Gly Asp Trp Xaa
1               5

( 2 ) INFORMATION FOR SEQ ID NO:3:

( i ) SEQUENCE CHARACTERISTICS:
    ( A ) LENGTH: 6 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note="SEE SEQ ID NO:1"

( i x ) FEATURE:
    ( A ) NAME/KEY: Modified-site
    ( B ) LOCATION: 6
    ( D ) OTHER INFORMATION: /label=NH2

( x i ) SEQUENCE DESCRIPTION: SEQ ID NO:3:

Xaa Lys Gly Asp Trp Xaa
1               5

( 2 ) INFORMATION FOR SEQ ID NO:4:

( i ) SEQUENCE CHARACTERISTICS:
    ( A ) LENGTH: 6 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note="pyrrolidine-3-carboxylic
        acid"

( i x ) FEATURE:
    ( A ) NAME/KEY: Modified-site
    ( B ) LOCATION: 6
    ( D ) OTHER INFORMATION: /label=OH ( x i ) SEQUENCE DESCRIPTION: SEQ ID NO:4:

Xaa Lys Gly Asp Trp Xaa
1               5

( 2 ) INFORMATION FOR SEQ ID NO:5:

( i ) SEQUENCE CHARACTERISTICS:
    ( A ) LENGTH: 6 amino acids
    ( B ) TYPE: amino acid
    ( C ) STRANDEDNESS: single
    ( D ) TOPOLOGY: linear (i i) MOLECULE TYPE: peptide (i x) FEATURE:
    (A) NAME/KEY: Modified-site
    (B) LOCATION: 1
    (D) OTHER INFORMATION: /note="SEE SEQ ID NO:4"

(i x) FEATURE:
    (A) NAME/KEY: Modified-site
    (B) LOCATION: 6
    (D) OTHER INFORMATION: /label=NH2

(x i) SEQUENCE DESCRIPTION: SEQ ID NO:5:

Xaa Arg Gly Asp Trp Xaa
1               5

(2) INFORMATION FOR SEQ ID NO:6:

(i) SEQUENCE CHARACTERISTICS:
    (A) LENGTH: 6 amino acids
    (B) TYPE: amino acid
    (C) STRANDEDNESS: single
    (D) TOPOLOGY: linear (i i) MOLECULE TYPE: peptide (i x) FEATURE:
    (A) NAME/KEY: Modified-site
    (B) LOCATION: 1
    (D) OTHER INFORMATION: /note="pyridine-4-carboxylic acid"

(i x) FEATURE:
    (A) NAME/KEY: Modified-site
    (B) LOCATION: 6
    (D) OTHER INFORMATION: /label=OH (x i) SEQUENCE DESCRIPTION: SEQ ID NO:6:

Xaa Arg Gly Asp Trp Xaa
1               5

(2) INFORMATION FOR SEQ ID NO:7:

(i) SEQUENCE CHARACTERISTICS:
    (A) LENGTH: 6 amino acids
    (B) TYPE: amino acid
    (C) STRANDEDNESS: single
    (D) TOPOLOGY: linear (i i) MOLECULE TYPE: peptide (i x) FEATURE:
    (A) NAME/KEY: Modified-site
    (B) LOCATION: 1
    (D) OTHER INFORMATION: /note="SEE SEQ ID NO:6"

(i x) FEATURE:
    (A) NAME/KEY: Modified-site
    (B) LOCATION: 6
    (D) OTHER INFORMATION: /label=OH (x i) SEQUENCE DESCRIPTION: SEQ ID NO:7:

Xaa Lys Gly Asp Trp Xaa
1               5

(2) INFORMATION FOR SEQ ID NO:8:

(i) SEQUENCE CHARACTERISTICS:
    (A) LENGTH: 6 amino acids
    (B) TYPE: amino acid
    (C) STRANDEDNESS: single
    (D) TOPOLOGY: linear (i i) MOLECULE TYPE: peptide (ix) FEATURE:
    (A) NAME/KEY: Modified-site
    (B) LOCATION: 1
    (D) OTHER INFORMATION: /note="quinoline-4-carboxylic acid"

(ix) FEATURE:
    (A) NAME/KEY: Modified-site
    (B) LOCATION: 6
    (D) OTHER INFORMATION: /label=OH (xi) SEQUENCE DESCRIPTION: SEQ ID NO:8:

Xaa Arg Gly Asp Trp Xaa
1               5

(2) INFORMATION FOR SEQ ID NO:9:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note="SEE SEQ ID NO:8"

(ix) FEATURE:
        (A) NAME/KEY: Modified-site
        (B) LOCATION: 6
        (D) OTHER INFORMATION: /label=OH (xi) SEQUENCE DESCRIPTION: SEQ ID NO:9:

Xaa Lys Gly Asp Trp Xaa
1               5

(2) INFORMATION FOR SEQ ID NO:10:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (ix) FEATURE:
        (A) NAME/KEY: Modified-site
        (B) LOCATION: 1
        (D) OTHER INFORMATION: /note="H2N—(CH2)2—CO"

(ix) FEATURE:
        (A) NAME/KEY: Modified-site
        (B) LOCATION: 6
        (D) OTHER INFORMATION: /label=OH (xi) SEQUENCE DESCRIPTION: SEQ ID NO:10:

Xaa Lys Gly Asp Trp Xaa
1               5

(2) INFORMATION FOR SEQ ID NO:11:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide ( i x ) FEATURE:
    ( A ) NAME/KEY: Modified-site
    ( B ) LOCATION: 1
    ( D ) OTHER INFORMATION: /note="H2N—(CH2)3—CO"

( i x ) FEATURE:
    ( A ) NAME/KEY: Modified-site
    ( B ) LOCATION: 6
    ( D ) OTHER INFORMATION: /label=OH ( x i ) SEQUENCE DESCRIPTION: SEQ ID NO:11:

Xaa Arg Gly Asp Trp Xaa
1               5

( 2 ) INFORMATION FOR SEQ ID NO:12:

( i ) SEQUENCE CHARACTERISTICS:
    ( A ) LENGTH: 6 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note="SEE SEQ ID NO:11"

( i x ) FEATURE:
    ( A ) NAME/KEY: Modified-site
    ( B ) LOCATION: 6
    ( D ) OTHER INFORMATION: /label=OH ( x i ) SEQUENCE DESCRIPTION: SEQ ID NO:12:

Xaa Lys Gly Asp Trp Xaa
1               5

( 2 ) INFORMATION FOR SEQ ID NO:13:

( i ) SEQUENCE CHARACTERISTICS:
    ( A ) LENGTH: 6 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Modified-site
    ( B ) LOCATION: 1
    ( D ) OTHER INFORMATION: /note="H2N—(CH2)4—CO"

( i x ) FEATURE:
    ( A ) NAME/KEY: Modified-site
    ( B ) LOCATION: 6
    ( D ) OTHER INFORMATION: /label=OH ( x i ) SEQUENCE DESCRIPTION: SEQ ID NO:13:

Xaa Arg Gly Asp Trp Xaa
1               5

( 2 ) INFORMATION FOR SEQ ID NO:14:

( i ) SEQUENCE CHARACTERISTICS:
    ( A ) LENGTH: 6 amino acids
    ( B ) TYPE: amino acid
    ( C ) STRANDEDNESS: single
    ( D ) TOPOLOGY: linear ( i i ) MOLECULE TYPE: peptide ( i x ) FEATURE:
    ( A ) NAME/KEY: Modified-site (B) LOCATION: 1
(D) OTHER INFORMATION: /note="H2N—(CH2)5—CO"

(ix) FEATURE:
(A) NAME/KEY: Modified-site
(B) LOCATION: 6
(D) OTHER INFORMATION: /label=OH (xi) SEQUENCE DESCRIPTION: SEQ ID NO:14:

Xaa Arg Gly Asp Trp Xaa
1               5

(2) INFORMATION FOR SEQ ID NO:15:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 1
(D) OTHER INFORMATION: /note="SEE SEQ ID NO:14"

(ix) FEATURE:
(A) NAME/KEY: Modified-site
(B) LOCATION: 6
(D) OTHER INFORMATION: /label=OH (xi) SEQUENCE DESCRIPTION: SEQ ID NO:15:

Xaa Lys Gly Asp Trp Xaa
1               5

(2) INFORMATION FOR SEQ ID NO:16:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 1
(D) OTHER INFORMATION: /note="SEE SEQ ID NO:14"

(ix) FEATURE:
(A) NAME/KEY: Modified-site
(B) LOCATION: 6
(D) OTHER INFORMATION: /label=NH2

(xi) SEQUENCE DESCRIPTION: SEQ ID NO:16:

Xaa Lys Gly Asp Trp Xaa
1               5

(2) INFORMATION FOR SEQ ID NO:17:

(i) SEQUENCE CHARACTERISTICS:
(A) LENGTH: 6 amino acids
(B) TYPE: amino acid
(C) STRANDEDNESS: single
(D) TOPOLOGY: linear (ii) MOLECULE TYPE: peptide (ix) FEATURE:
(A) NAME/KEY: Modified-site
(B) LOCATION: 1
(D) OTHER INFORMATION: /note="H2N—(CH2)6—CO"

( i x ) FEATURE:
    ( A ) NAME/KEY: Modified-site
    ( B ) LOCATION: 6
    ( D ) OTHER INFORMATION: /label=OH ( x i ) SEQUENCE DESCRIPTION: SEQ ID NO:17:

Xaa Arg Gly Asp Trp Xaa
1               5

( 2 ) INFORMATION FOR SEQ ID NO:18:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="SEE SEQ ID NO:17"

( i x ) FEATURE:
        ( A ) NAME/KEY: Modified-site
        ( B ) LOCATION: 6
        ( D ) OTHER INFORMATION: /label=NH2

( x i ) SEQUENCE DESCRIPTION: SEQ ID NO:18:

Xaa Lys Gly Asp Trp Xaa
1               5

( 2 ) INFORMATION FOR SEQ ID NO:19:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="H2N—(CH2)7—CO"

( i x ) FEATURE:
        ( A ) NAME/KEY: Modified-site
        ( B ) LOCATION: 6
        ( D ) OTHER INFORMATION: /label=NH2

( x i ) SEQUENCE DESCRIPTION: SEQ ID NO:19:

Xaa Arg Gly Asp Trp Xaa
1               5

( 2 ) INFORMATION FOR SEQ ID NO:20:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( i x ) FEATURE:
        ( A ) NAME/KEY: Modified-site
        ( B ) LOCATION: 1
        ( D ) OTHER INFORMATION: /note="H2N—CH2—CH(CH3)—CO"

( i x ) FEATURE:

(A) NAME/KEY: Modified-site
(B) LOCATION: 6
(D) OTHER INFORMATION: /label=OH (xi) SEQUENCE DESCRIPTION: SEQ ID NO:20: